(12) United States Patent
Ma (10) Patent No.: US 9,056,147 B2
(45) Date of Patent: Jun. 16, 2015

(54) UV DISINFECTION SYSTEM FOR NEEDLELESS CONNECTOR

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/904,295

(22) Filed: May 29, 2013

(65) Prior Publication Data

US 2013/0323120 A1 Dec. 5, 2013

Related U.S. Application Data (60) Provisional application No. 61/653,932, filed on May 31, 2012.

(51) Int. Cl.
*A61L 2/10* (2006.01)
*A61L 2/24* (2006.01)

(52) U.S. Cl.
CPC ... *A61L 2/10* (2013.01); *A61L 2/24* (2013.01); *A61L 2202/14* (2013.01); *A61L 2202/24* (2013.01)

(58) Field of Classification Search
CPC .......................................................... A61L 2/10
USPC ........................................ 422/24; 250/455.11
See application file for complete search history.

(56) References Cited

U.S. PATENT DOCUMENTS

| | | | |
|---|---|---|---|
| 7,211,813 B2 * | 5/2007 | Jensen ...................... 250/504 H |
| 7,213,603 B2 * | 5/2007 | Pinsky .......................... 132/310 |
| 7,918,229 B2 * | 4/2011 | Cumbie et al. ................ 128/898 |
| 8,226,887 B2 * | 7/2012 | Harmon et al. ................. 422/24 |
| 2007/0176117 A1 * | 8/2007 | Redmond et al. ........ 250/455.11 |
| 2008/0219883 A1 * | 9/2008 | Thur et al. ...................... 422/22 |
| 2008/0219899 A1 | 9/2008 | Deshays |
| 2008/0280260 A1 * | 11/2008 | Belikov et al. ................ 433/215 |
| 2009/0018485 A1 * | 1/2009 | Krespi et al. .................... 604/20 |
| 2009/0257910 A1 | 10/2009 | Segal |
| 2010/0145721 A1 | 6/2010 | Deshays |
| 2011/0125013 A1 | 5/2011 | Neer |
| 2011/0197921 A1 | 8/2011 | Rubin et al. |
| 2011/0213339 A1 * | 9/2011 | Bak ................................ 604/523 |
| 2011/0224649 A1 | 9/2011 | Duane et al. |
| 2011/0284024 A1 | 11/2011 | Trebella et al. |
| 2011/0308034 A1 * | 12/2011 | Powers et al. ................... 15/324 |

FOREIGN PATENT DOCUMENTS

| | | | |
|---|---|---|---|
| WO | 02/074350 A1 | 9/2002 |
| WO | 02/102421 A1 | 12/2002 |
| WO | 2011/107540 A1 | 9/2011 |

* cited by examiner

*Primary Examiner* — Sean E Conley
(74) *Attorney, Agent, or Firm* — Jeanne Lukasavage; Craig Metcalf; Kirton McConkie (57) ABSTRACT

A device is presented for disinfecting needleless connectors. The device has a housing that contains a UV light source. The UV light source is operably connected to a power source. The housing has a receptacle configured to selectively receive a shield. The shield has an inner reflective chamber with an internal surface that reflects UV light. In use, the UV light source can illuminate a needleless connector inserted within the shield.

20 Claims, 8 Drawing Sheets

UV DISINFECTION SYSTEM FOR NEEDLELESS CONNECTOR

RELATED APPLICATION

This application claims priority to U.S. Provisional Patent Application Ser. No. 61/653,932, filed May 31, 2012 and titled SYSTEM AND METHODS FOR DISINFECTING NEEDLELESS CONNECTORS, which is incorporated herein in its entirety.

BACKGROUND OF THE INVENTION

The present invention relates to systems and methods for disinfecting needleless connectors. In particular, the present invention relates to a disinfection device that disinfects using an ultraviolet light source.

One of the major challenges of modern medical treatment is control of infection and the spread of microbial organisms. One area where this challenge is constantly presented is in infusion therapy procedures. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, and maintain blood pressure and heart rhythm, or many other clinically significant uses.

Infusion therapy is facilitated by an intravenous (IV) administration set. The IV administration set may access a patient's peripheral or central vasculature. The IV administration set may be indwelling for short term (days), moderate term (weeks), or long term (months to years). The IV administration set may be used for continuous infusion therapy or for intermittent therapy.

A common component of an IV administration set is a plastic catheter that is inserted into a patient's vein. The IV administration set may further include various connectors and fittings that further facilitate intravenous access and communication. For example, an IV administration set may include a needleless Luer adapter to which other medical devices may be attached. Commonly, an IV administration set comprises one or more vascular access devices that may be attached to another vascular access device, close the vascular access device, and allows for intermittent infusion or injection of fluids and pharmaceuticals. An IV administration set may further include a connector (including a Luer connector) with a septum for closing the system. The septum may be opened with a needleless connector, such as a blunt cannula or a male Luer of a medical device.

An IV administration set may serve as a nidus of infection, resulting in a disseminated BSI (blood stream infection). In some instances, this may be caused by insufficient disinfection of the various connectors and other access components of the IV administration set. Generally, disinfection of needleless connectors and other access components of the IV administration set are accomplished through manual scrubbing using a disinfection swab or pad. However this process varies greatly from clinician to clinician both in terms of duration and contact forces. These variations lead to inconsistent disinfection which may encourage bacterial growth and infection.

Thus, while techniques currently exist for disinfecting needleless connectors and components of an IV administration set, challenges still exist. Accordingly, it would be an improvement in the art to augment or even replace current techniques with other techniques.

BRIEF SUMMARY OF THE INVENTION

The present invention relates to systems and methods for disinfecting needleless connectors. In particular, the present invention relates to a disinfection device that disinfects using an ultraviolet light source. In some aspects of the invention, a disinfecting device includes a housing that contains an ultraviolet (UV) light source. The UV light source is operably connected to a power source. The housing has a receptacle configured to selectively receive a shield. The shield has an inner reflective chamber with an internal surface that reflects UV light. In use, the UV light source can illuminate a needleless connector inserted within the shield, thereby resulting in disinfection of the needleless connector.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The present invention relates to systems and methods for disinfecting needleless connectors. In particular, the present invention relates to a disinfection device having a UV source and a socket configured to receive a needleless connector, wherein a disposable shield is interposed between the needleless connector and the UV source, and wherein the needleless connector is disinfected upon exposure to the UV source.

As used herein, the term "disinfection" is used to denote a level of sanitation that is free from infection or free from microorganisms which are capable of promoting infection in the patient.

As used herein, the term "disinfectant" is used to denote an agent that destroys vegetative forms of harmful microorganisms such as bacteria, fungi, yeasts, viruses and other harmful pathogens.

As used herein, the term "needleless connector" is used to denote a medical coupler which is used as part of an intravenous assembly. In some instances, a needleless connector comprises a Luer adapter or a male Luer. In other instances, a needleless connector comprises a PRN connector. An example of a needleless connector is the Q-Syte™ luer access port from Becton, Dickinson. Further, in some instances a needleless connector comprises a port or valve of a section of intravenous tubing or a connector thereof. One having skill in the art will appreciate that the systems and methods of the present invention may be adapted for use with various other types of connectors and other devices for which automated disinfection is desirable.

As used herein, the term "UV light source" is used to denote a lamp, a light-emitting diode (LED), a laser, or another similar technology that is capable of emitting wavelengths in the range of 290 nm-100 nm, and/or which are capable of killing pathogens present on a needleless connector. In some instances, a UV light source denotes a LED lamp configured to emit UV-C wavelengths.

Figure 1:
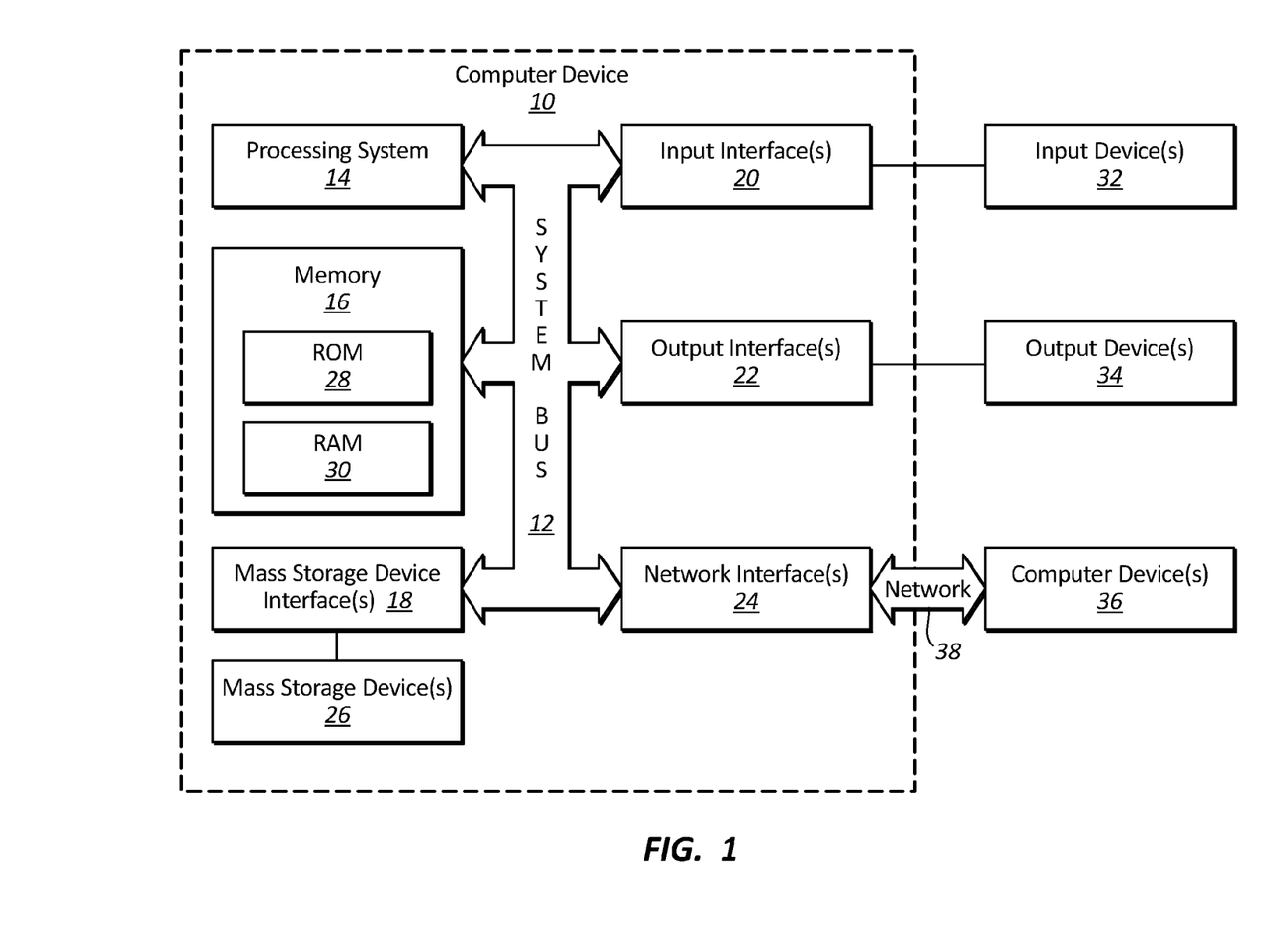
FIG. 1 shows a flow chart of a representative system that provides a suitable operating environment in which various embodiments of the present invention may be implemented.
Figure 2:
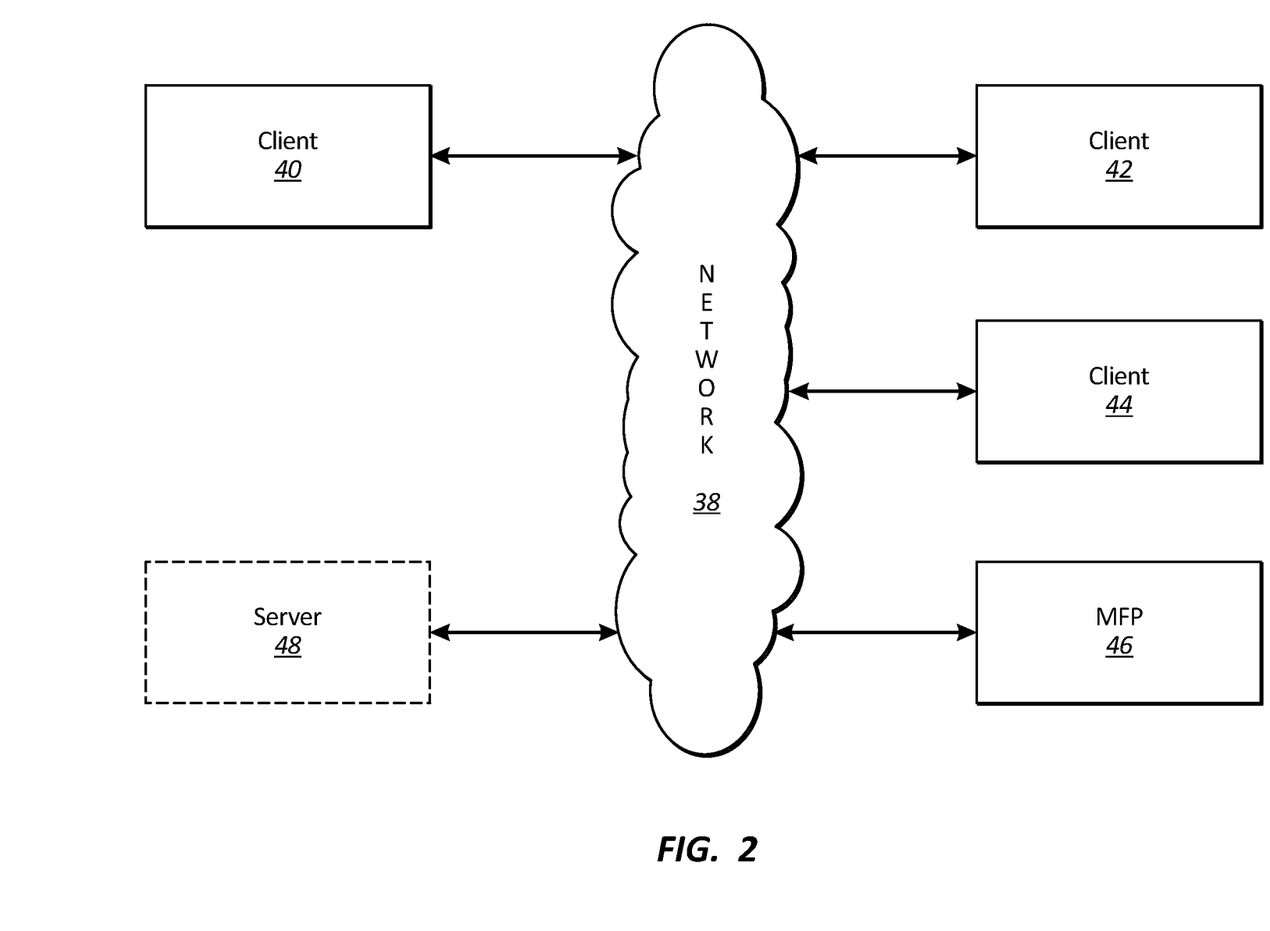
FIG. 2 shows a flow chart of a representative networking system that provides a suitable environment in which various embodiments of the present invention may be implemented.

FIGS. 1 and 2, and the corresponding discussion, provide a general description of a suitable operating environment in which embodiments of the invention may be implemented. One skilled in the art will appreciate that embodiments of the invention may be practiced by one or more computing devices and in a variety of system configurations, including in a networked configuration. However, while the methods and processes of the present invention have proven to be particularly useful in association with a system comprising a general purpose computer, embodiments of the present invention include utilization of the methods and processes in a variety of environments, including embedded systems with general purpose processing units, digital/media signal processors (DSP/MSP), application specific integrated circuits (ASIC), standalone electronic devices, and other such electronic environments.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative system for implementing embodiments of the invention includes computer device 10, which may be a general-purpose or special-purpose computer. For example, computer device 10 may be a personal computer, a notebook computer, a personal digital assistant ("PDA") or other hand-held device, a workstation, a minicomputer, a mainframe, a supercomputer, a multi-processor system, a network computer, a processor-based consumer electronic device, a smart phone, a position identifier, a ball collector, or the like.

Computer device 10 may include a system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, thumb drives, solid state memory, a universal serial bus or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, thumb drive tape drives and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a firewire (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen, a speaker, a printer, a multi-functional peripheral, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices (illustrated as multifunctional peripheral (MFP) MFP 46) across network 38. While FIG. 2 illustrates an embodiment that includes a client 40, two additional clients, client 42 and client 44, one peripheral device, MFP 46, and optionally a server 48, connected to network 38, alternative embodiments include more or fewer clients, more than one peripheral device, no peripheral devices, no server 48, and/or more than one server 48 connected to network 38.

Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet.

Figure 3:
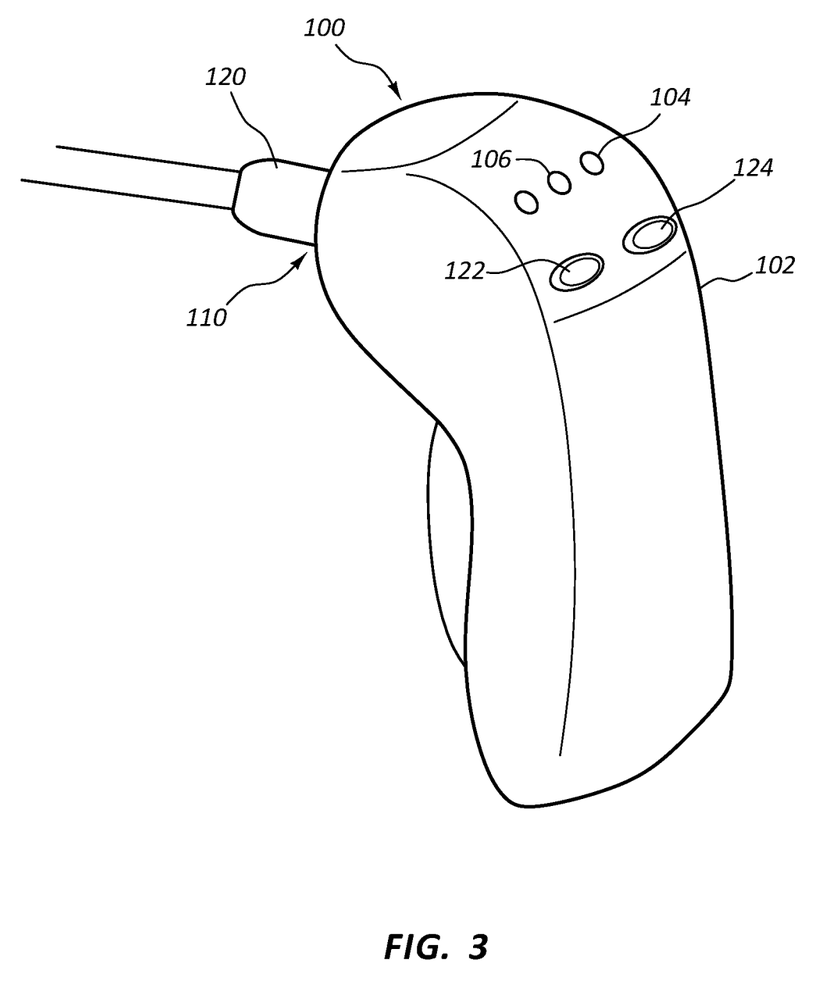
FIG. 3 is a perspective view of a handheld disinfection device in accordance with a representative embodiment of the present invention.

Referring now to FIG. 3, an implementation of a disinfection device 100 is shown. In some embodiments, a disinfection device 100 is provided as a handheld unit, wherein the disinfection device comprises a housing 102 which is sized and configured to be held in the hand of the user during disinfection of a needleless connector 120. Housing 102 of disinfection device 100 may include any size, shape and/or configuration as may be desirable. For example, in some embodiments disinfection device 100 comprises a stationary tabletop unit.

In some embodiments, housing 102 of disinfection device 100 further comprises one or more status indicators 104 that indicate a level of disinfection of needleless connector 120. For example, in some instances, status indicators 104 include one or more lights 106 that are configured to provide information to a user. In some instances, lights 106 may blink to indicate a stage or level of disinfection for needleless connector 120. Lights 106 may further comprise two or more colors, wherein a color indicates a stage or level of disinfection for needleless connector 120. For example, in some embodiments a red light indicates incomplete or unsatisfactory disinfection of needleless connector 120. Further, a yellow light may indicate an intermediary or active process of disinfection for needleless connector 120. Further still, a green light may indicate a satisfactory or complete disinfection for needleless connector 120.

Lights 106 may further be programmed to blink or otherwise demonstrates a lighted pattern to further communicate a status of disinfection device 100. For example, in some embodiments lights 106 may be programmed to demonstrate a lighted pattern to indicate a low battery. Lights 106 may further be programmed to demonstrate and error or mechanical malfunction. In some instances, lights 106 may be programmed to indicate that disinfection device 100 is ready to receive needleless connector 120.

In place of lights 106, status indication 104 can alternatively include a display screen (not shown), such as a LCD screen, that displays operation times, disinfection status, battery levels, or other such status notifications. Moreover, a variety of other alternative status indicators 104 can be utilized with disinfection device 100.

In some embodiments, disinfection device 100 includes a disposable shield 110 that is selectively connected to housing 102 at a location that facilitates easy access for needleless connector 120. In some instances, shield 110 is positioned opposite of status indicators 104 thereby permitting the user to access shield 110 with needleless connector 120 while maintaining visualization a status indicators 104. Shield 110 may be accessed as a user holds disinfection device 100 in their hand while aligning and contacting needleless connector 120 with shield 110 using the user's other hand.

Figure 4:
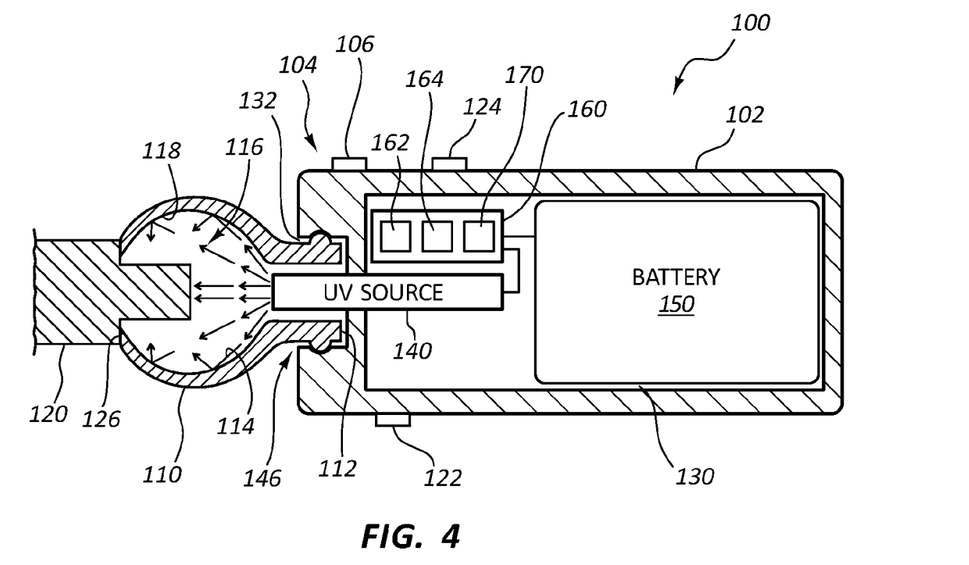
FIG. 4 is a cross sectioned view of a disinfector device in accordance with a representative embodiment of the present invention.

Referring now to FIGS. 3 and 4, disposable shield 110 comprises a first end that is configured to couple to socket or receptacle 146 of housing 102. In some embodiments, socket 146 comprises an opening 132 that is sized and configured to receive and retain shield 110. The first end of disposable shield 110 further comprises a proximal opening 112 that is sized and configured to receive a UV light source 140. Shield 110 further comprises a second end having a distal opening 126 that is sized and configured to compatibly receive a portion of a needleless connector 120. In some instances, the interface connections between shield 110, socket 146, UV light source 140, proximal opening 126 and needleless connector 120 provide a closed system that prevents leakage of light from UV light source 140 to the exterior environment.

An activation button 124 initiates a disinfecting operation in which UV light is emitted from UV light source 140 into shield 110. Pressing activation button 124 can initiate continuous disinfection operation until activation button 124 is pressed again. Alternatively, activation button 124 can initiate the temporary disinfection operation. A temporary disinfection operation can last approximately 1, 2, 3, 4, 5, 10, 15, 20, 30 or more than 30 seconds. During disinfection, shield 110 reflects the UV light from UV light source 140 onto each of the external surfaces of needleless connector 120 to disinfect the connector. After exposure for a predetermined time, the needleless connector 120 is disinfected and ready for use. The user may then remove needleless connector 120 from shield 110 thereby completing the disinfection process.

In some embodiments, an ejection button 122 on housing 102 can activate an ejector, or detachment mechanism (not shown) that ejects the shield 110 from the disinfection device 100. Ejected shield 110 can remain attached to the needleless connector 120 as a physical contamination barrier or it may be removed from the needleless connector 120 and released into the trash.

With continued reference to FIG. 4, a cross-section top view of disinfection device 100 is shown. In some embodiments, housing 102 comprises an interior 130 in which is housed various components of the device. For example, interior 130 houses a UV light source 140 that is positioned and configured to illuminate the interior of a shield 110 removably coupled to a distal end of the housing 102. The UV light source 140 can project out from an end surface of housing 104, as shown, or alternatively be flush or recessed within such a surface. Alternatively, the UV light source 140 may be protected from accidental damage by reside within a protective window. The protective window would be transparent to UV light. UV light source 140 may comprise any device or technology capable of emitting light waves capable of killing pathogens. In some instances, UV light source 140 comprises a lamp capable of emitting wavelengths in the range of 290 nm-100 nm. In other instances, UV light source 140 comprises a florescent lamp, a light-emitting diode (LED), or a laser. For instance, a UV-C LED can provide the disinfecting illumination while having a low power consumption and robust structure. While one UV light source 140 may be effectively utilized, some embodiments may incorporate multiple UV light sources 140 into disinfection device 100.

In some embodiments, housing 102 includes a distal opening 132 forming a socket or receptacle 146 that is accessible to the user. Receptacle 146 is sized and configured to compatibly receive and retain at least a proximal portion of shield 110. In some embodiments, shield 110 is removable and disposable. In other embodiments, shield 110 is reusable. Shield 110 can be shaped and sized to form an inner reflection chamber 116 having a length and diameter configured to compatibly receive needleless connector 120. Reflection chamber 116 can include a proximal opening 112 into which UV light source 140 can be inserted or UV light can otherwise be illuminated through. Moreover, reflection chamber 116 can include a distal opening 126 configured to compatibly receive needleless connector 120 without permitting the escape of substantial amounts of UV illumination.

Shield 110 may be manufactured using various materials. Material used to produce a disposable shield 110 may be selected for its low cost, recyclability, and/or environmental impact. Non-limiting examples of materials used to manufacture shield 110 include polymers (e.g., plastics), composites, and/or metals. In some embodiments, the selected materials provide sufficient rigidity to shield 110 to substantially maintain the shape of reflection chamber 116 against pressure from housing 102, needleless connector 120, and other external forces (e.g., forces used to insert shield 110 into receptacle 146). Moreover, in some embodiments the selected material provide sufficient flexibility to withstand these forces and/or so that the opening 126 can substantially conform about needleless connector 120.

In some embodiments, shield 110 further includes an interior reflective surface 118 that reflects light 114 within reflection chamber 116 so that each surface of needleless connector 120 is exposed to the UV light 114. Accordingly, the interior surface of shield 110 may include various shapes, sizes and geometries, including a spherical or other suitable geometry configured to achieve optimal light scattering or distribution within the interior of shield 110. In some instances, shield 110 is manufactured using a reflective material or includes a reflective lining or coating that forms interior reflective surface 118. In some configurations, reflective surfaces 118 are diffusive to ensure substantially complete UV coverage. Shield 110 may thus limit or eliminate UV exposure to an operating clinician and patients in proximity to disinfecting device 100.

UV light source 140 is generally provided as a means for providing UV illumination to disinfect needleless connector 120. In some instances, disinfection device 100 includes a power control (not shown) whereby to regulate the power provided to UV source 140. Increasing the power of a UV light source 140 may increase illumination intensity and thereby accelerate a disinfection process. Accordingly, some implementations of the infecting device 100 include a power control which regulates or modifies power supplied to the UV light source from a battery 150 or other power source. Supplied power can be continuous, pulsed, or otherwise varied.

Disinfection device 100 may further comprise a printed circuit board 160 that comprises various monitoring and feedback circuitry to control proper disinfection of needleless connector 120. Electronic circuit board 160 can be electronically coupled to battery 150 and/or UV light source 140. For example, in some embodiments printed circuit board 160 comprises a power sensor 162 that is configured to monitor and measure power supplied to UV source 140. Printed circuit board 160 may further comprise a status indicator controller 170. Status indicator controller 170 can control status indicator 104, including lights 106.

Printed circuit board 160 may further comprise a timer 170 used to measure or count a time lapse or interval over which UV illumination is provided to shield 110. In some instances, sufficient disinfection is a factor of illumination power and time. For example, in some embodiments, complete disinfection requires that the minimum power threshold be maintained for a minimal length of time, such as from about 1 second to about 15 seconds. In some embodiments, complete disinfection requires that the minimum power threshold be maintained from a minimum length of time of about 5 seconds or less. Thus, timer 170 can be used to control the length of time during which the motor operates.

Figure 5:
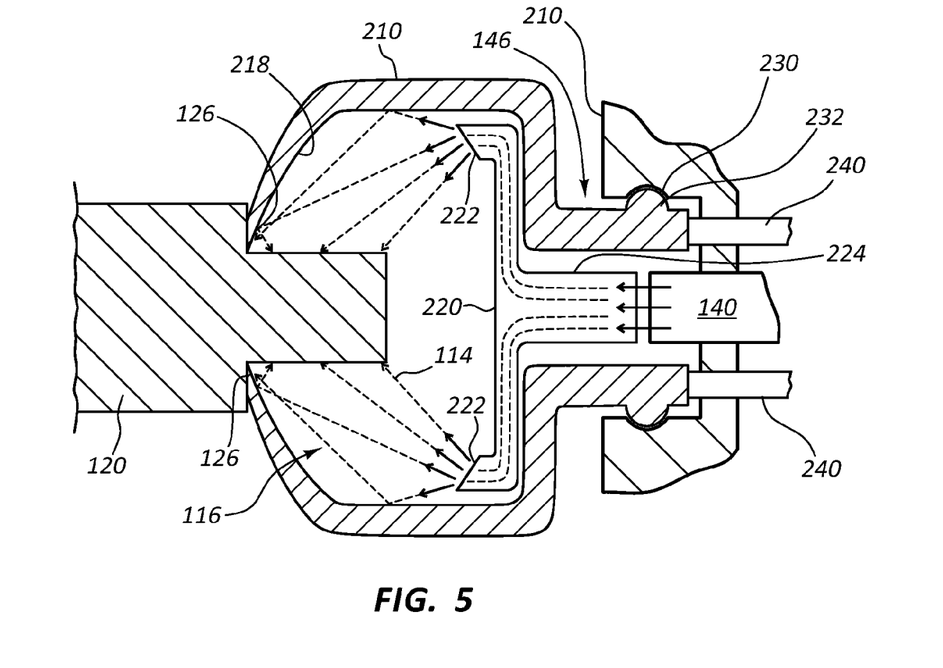
FIG. 5 is a cross-section view of a shield and a needleless connector in accordance with a representative embodiment of the present invention.

Reference will now be made to FIG. 5, which illustrates an embodiment of a shield 210 disposed within receptacle 146. Shield 210 includes a reflection chamber 116 that engages at least a portion of needleless connector 120. Some embodiments of shield 210 includes a diffuser, spreader, light tube, or light pipe 220 used to disperse, steer, and/or direct UV light within reflection chamber 116. For example, light pipe 220 can include a stem portion 224 adjacent to or abutting UV light source 140. UV light can be directed along the stem portion 224 and then along two or more branch portions 222. Branch portions 222 can direct beams of UV light 114 toward multiple sides of needleless connector 120 to directly or indirectly illuminate substantially all exterior surfaces, including threaded surfaces, of needleless connector 120. Thus, a light pipe or other optical device can assist to completely illuminate needleless connector 120.

As further shown in FIG. 5, shield 210 can include one or more attachment features 232 that can be used to selectively couple shield 210 within recess 146 of housing 102. As shown, attachment features 232 may include a protrusion, latch, hook, or other such protruding structure that can be latched to or otherwise attached within receptacle 142. Conversely, in other embodiments, attachment features 232 comprises an indent, an annular or partial recess or groove, or other structure that can be clasped or otherwise attached within recess 146. In some embodiments, recess 146 includes a corresponding attachment feature 230 configured to mate with and secure attachment features 232 of shield 208.

In some embodiments, one or more ejectors 240 are disposed within a proximal end of receptacle 146. Ejectors 240 may be one or more pistons or other movable structure that can selectively press distally against shield 210 until it is forced out receptacle 146. The distal force of ejector 240 can cause attachment features 230, 232 to disengage, releasing shield 210 from receptacle 146. As previously mentioned, ejection can be initiated when a user presses an ejection button (122 in FIG. 3). The ejected shield 110 can remain attached to the needleless connector 120 as a physical contamination barrier or it may be removed from the needleless connector 120 released into the trash.

Figure 6:
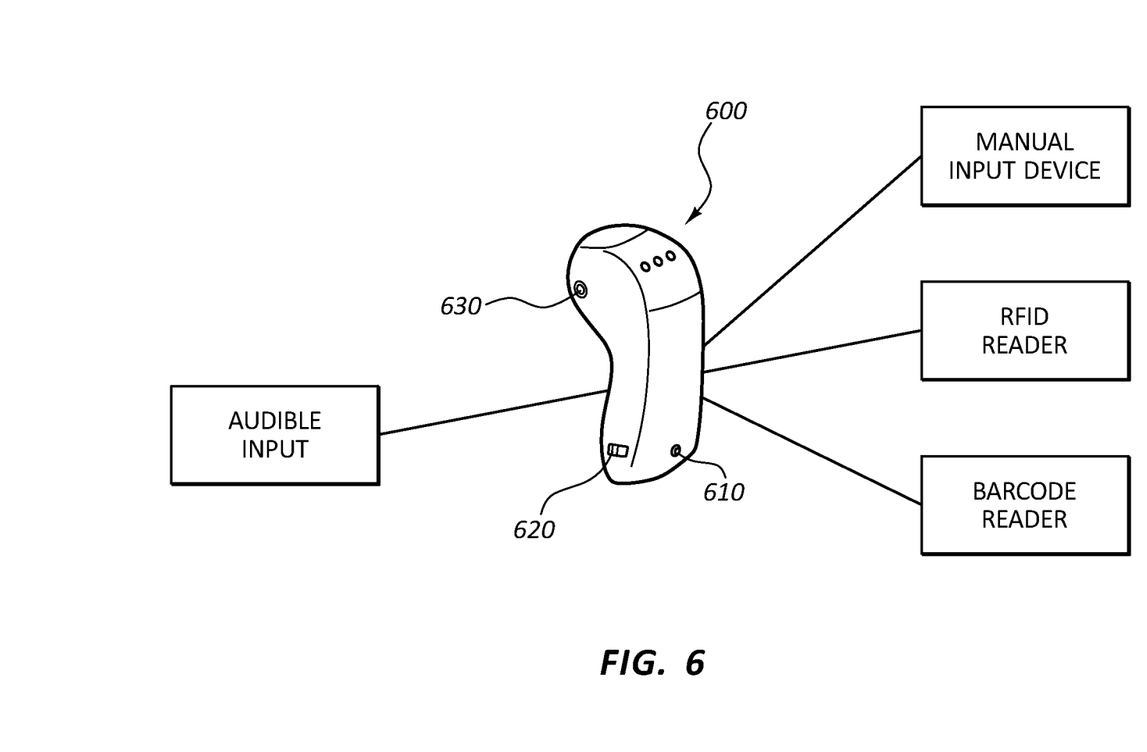
FIG. 6 is a perspective view of a handheld disinfection device further comprising input and output features in accordance with a representative embodiment of the present invention.

In some embodiments, disinfection device 600 further comprises an input interface 610 and an output interface 620 to facilitate collection and reporting of information related to a cleaning event of disinfection device 600, as shown in FIG. 6. For example, in some embodiments input interface 610 comprises a barcode scanner which is capable of reading a computer-readable barcode that is placed on a needleless connector, and/or an identification tag or label of the patient and/or the identification of the shield. In other embodiments, input interface 610 further comprises a magnetic card reader, or an optical camera which is capable of retrieving information stored within a magnetic stripe or a computer-readable code, respectively. For example, a patient may have an identification card having a magnetic stripe which contains the identity of the patient and other related medical information. The patient, the shield and/or needleless connector may further include a QR code which is capable of being detected and deciphered using an optical camera and computer-executable software configured to retrieve information from the QR code. In other embodiment, the patient, the shield and/or the needleless connector may further include RFID tag which can be read by a RFID reader on the disinfection device.

Some embodiments of the present invention further comprise a device or component of a device that includes a material, a coating, or a tag containing a material or coating that is configured to change color in response to prolonged exposure to air and/or a liquid. A color-changing material may be useful in communicating to a user a length of time for which the shield and/or needleless connector has been exposed to an unsterile environment. A color-changing material may also be useful in communicating to a user that the device or component has been previously used. In some instances, a device or component of the present invention is packaged in airtight packaging, thereby preserving an initial color of the color-changing material. Upon opening the airtight packaging, the color-changing material is exposed to air thereby changing the color of the device or component. This feature may prevent a device or component from being reused. This feature may also prevent an unsterile device or component from being used.

In some embodiments, information relating to the identity of the patient and the identity of the needleless adapter are retrieved and stored by input interface 610 prior to a disinfection event. In some instances, additional information relating to the disinfection event is further collected and stored in memory of the disinfection device. For example, disinfection device 600 may further collect and store information such as the date and time of the disinfection event, the identity of the clinician, and a final disinfection status of the needleless connector. Following the disinfection event, the collected and stored information is transferred to a remote computer device via output interface 620.

Output interface 620 may include any type or configuration of output which is capable of transferring stored information from disinfection device 600 to a remote computer device. For example, in some embodiments output interface 620 comprises a wireless antenna. In other embodiments, output interface 620 comprises an electrical connector, such as a universal serial bus. Output interface 620 may further comprise an RFID transmitter. Output interface 620 may further include a wireless link (e.g., WiFi, Bluetooth®, IR, RF, or other known wireless communication approaches, a direct wired connection (e.g. electrical wire or optical cable), or a direct connection via one or more direct lead contacts. Thus, output interface 620 facilitates communication between disinfection device 600 and a remote computer device, whereby information obtained by and stored on memory of disinfection device 600 may be transferred to a remote computer device for long-term storage.

Input and output interfaces 610 and 620 may be located at any position on the housing of disinfection device 600. In some embodiments, input and output interfaces are positioned such that a user may hold disinfection device 600 in their hand and still have access to the interfaces. Input and output interfaces 610 and 620 may further comprises a separate device that is operably connected to disinfection device 600 via a corded or wired connection, or a wireless connection. For example, input interface 610 may comprises a wireless antenna that receives a signal from barcode scanner that is wirelessly connected to input interface 610.

In some instances, information retrieved by disinfection device 600 is temporarily stored within memory of disinfection device 600. The stored information may subsequently be transferred to a remote computer device via output interface 620. In some embodiments, retrieved information is transferred to a remote computer device in real-time via output interface 620. Input and output interfaces 610 and 620 may further be used to retrieve, record, and report information regarding the identity of a patient, wherein the patient information is contained in a computer-readable format. In some instances, the processes of recording and reporting the retrieved information is automatic, thereby eliminating user error.

In some embodiments, information regarding the identity of the patient and/or the needleless connector is entered manually into disinfection device 600 or a remote computer device. For example, disinfection device 600 may include a keyboard. Disinfection device 600 may further include a microphone and transcription software, whereby a clinician may audibly enter information into disinfection device 600.

Disinfection device 600 may further be operably connected to a separate input device, whereby the clinician is able to input information into disinfection device 600 via the separate input device.

In some embodiments, the process of detecting a disinfection status, tracking a disinfection event, recording the disinfection event, and reporting the disinfection event may ensure compliance to proper cleaning procedures, thereby helping the clinical outcomes for patients and care providers. This information may further be stored in an electronic medical record (EMR) of the patient. As such, the disinfection event becomes part of the patient's medical history which may be accessible to other physicians and clinicians to assist in treatment of the patient. The information may further be accessed as part of an audit proceeding, such as a safety compliance audit. This information may further be accessed to assess areas, methods and techniques that may need revision to increase the quality and/or consistency of patient care.

Figure 7:
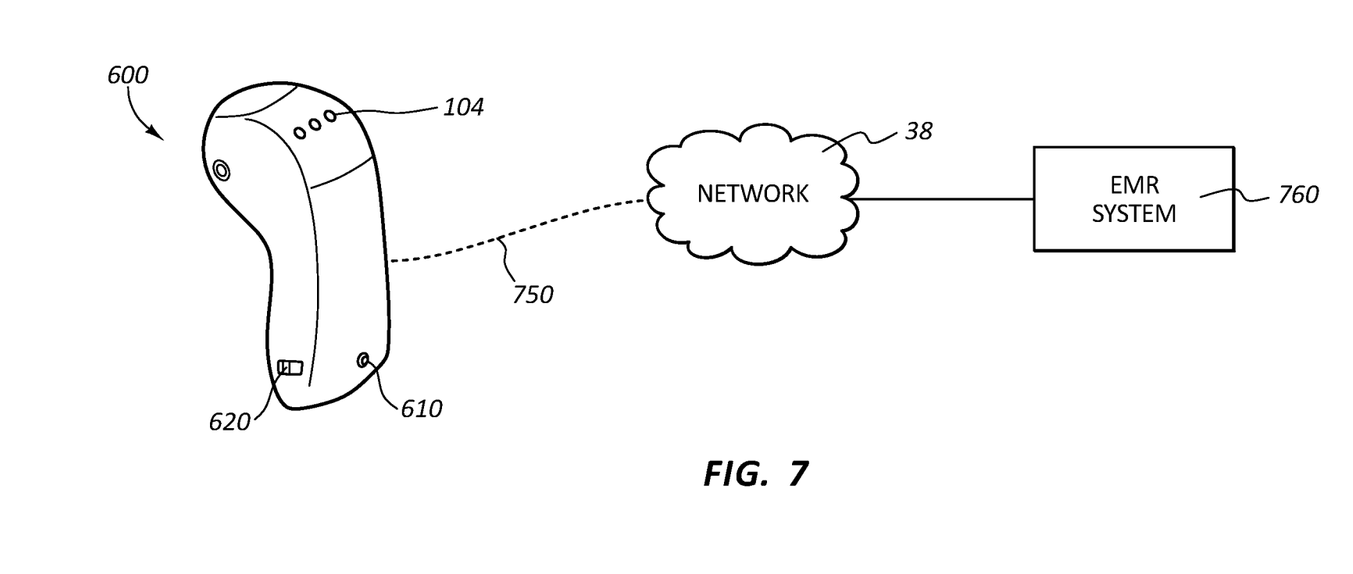
FIG. 7 is a diagrammatic view of a handheld disinfection device operably connected to an electronic medical record via a network in accordance with a representative embodiment of the present invention.

Referring now to FIG. 7, in some embodiments disinfection device 600 is operably connected to a network 38 via a hardwired and/or wireless link 750. In some embodiments, link 750 comprises a portion of output interface 620. When information is acquired by disinfection device 600, the information is transmitted to network 38 where the information is made accessible to various remote computer devices also operably connected to network 38. Further, in some embodiments acquired information is stored in a database, such as an EMR 760.

EMR 760 generally comprises a computerized medical record for a patient, as known in the art. In some embodiments, EMR 760 is configured to receive and store information relating to the disinfection event. For example, EMR 760 may receive information such as the date of the disinfection event, a final status of the disinfection event, the identity of the clinician who performed the disinfection event, the identity of the needleless connector, as well a time and/or duration of the disinfection event.

Network 38 may include a server on which a computer executable program is loaded having instructions for receiving, analyzing, and storing information received from disinfection device 600. Network 38 may further include network security software or other precautionary software as may be required to comply with Health Information Patient Privacy Act requirements. In some embodiments, network 38 comprises a local area network. In other embodiments, network 38 is a global area network.

Figure 8:
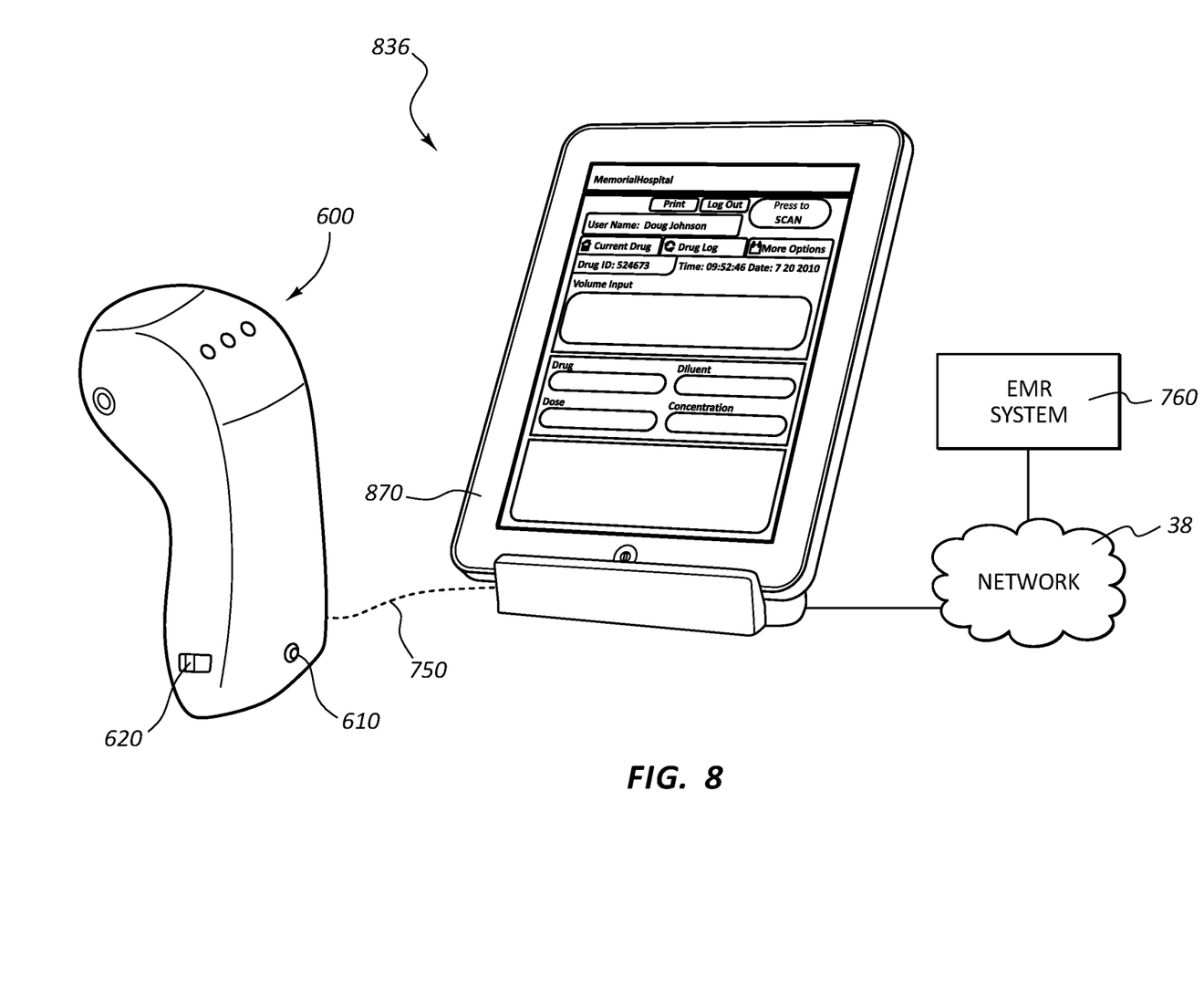
FIG. 8 is a diagrammatic view of a handheld disinfection device operably connected to an electronic medical record via a computer device and a network in accordance with a representative embodiment of the present invention.

In some configurations, disinfection device 600 is operably connected to network 38 via a processor unit 870 or other computer system, as shown in FIG. 8. Processor unit 870 receives and processes retrieved information from output interface 620 prior to storing the information in EMR 760. Processor unit 870 may include any type or form of computing device which is compatible with the teachings of the present invention. In some embodiments, processor unit 870 comprises a tablet computer. In other embodiments, processor unit 870 comprises a desktop computer. Processor unit 870 may further comprise a mainframe computer. Further still, in some embodiments processor unit 870 comprises a mobile smart device, such as a smartphone, a tablet computer, or personal digital assistant device.

Figure 9:
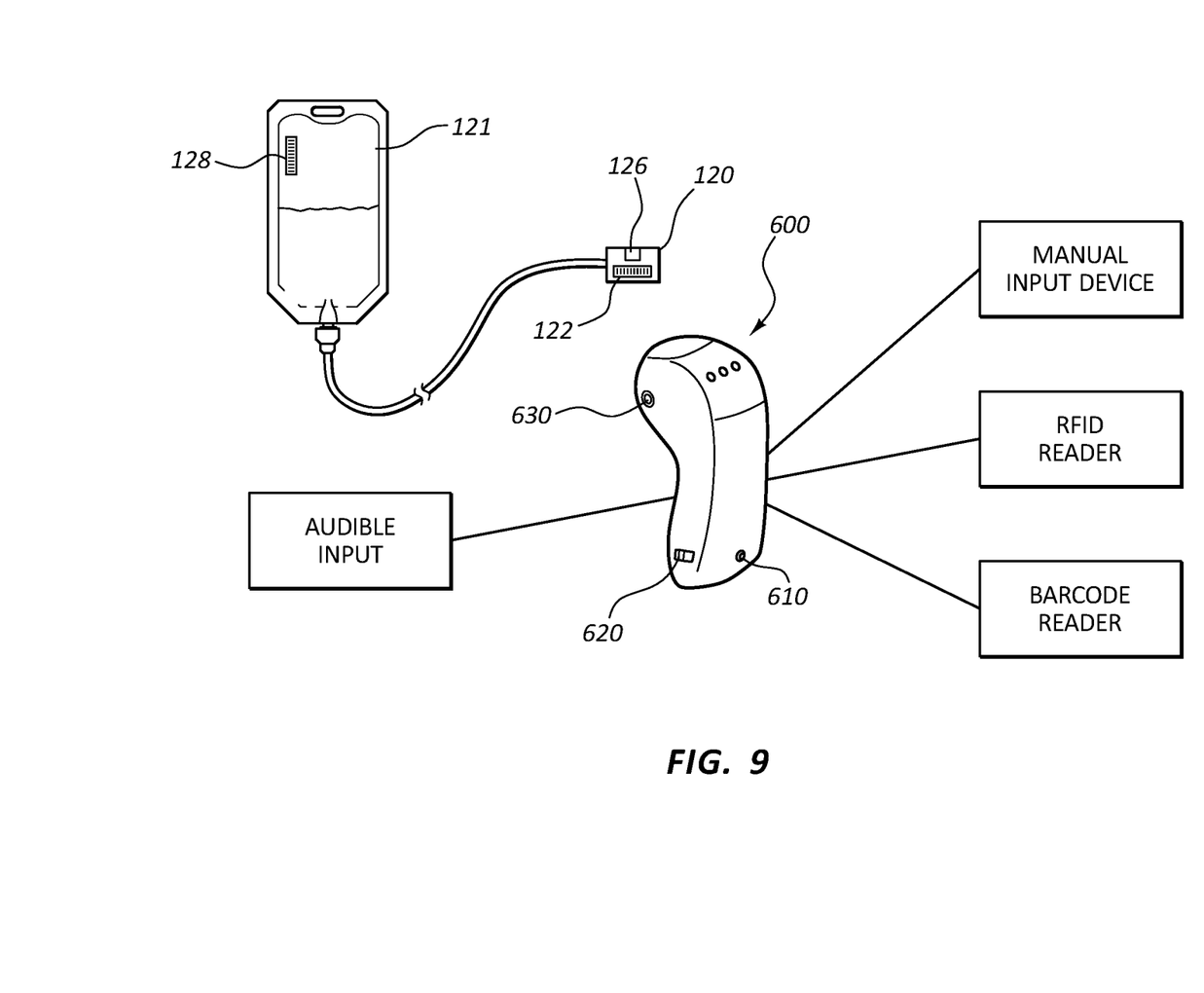
FIG. 9 is a diagrammatic view of a handheld disinfection device demonstrating various input and output features in accordance with a representative embodiment of the present invention.

Referring now to FIG. 9, disinfection device 600 may include various systems and/or methods by which information relating to needleless connector 120 may be collected and reported. For example, in some embodiments disinfection device 600 comprises input and output interfaces 610 and 620 which are capable of scanning a barcode 122 of needleless connector 120. Input and output interfaces 610 and 620 may further scan a barcode 128 of an IV fluid bag 121 coupled to needleless connector 120. In some instances, needleless connector 120 comprises an RFID chip 126. Accordingly, disinfection device 600 may include an RFID reader. Disinfection device 600 may further include an RFID transmitter whereby to report retrieved information to a computer device comprising an RFID receiver.

Input interface 610 may further comprise a microphone 630 whereby information is input by speaking the information into microphone 630. The information may subsequently be reported or transferred to a remote computer device by any of the various output interfaces 620 with which disinfection device 600 is equipped. Accordingly, various embodiments of the present invention provide a disinfection device having one or more input interfaces 610 and one or more output interfaces 620, whereby information is retrieved by one or more of the input interfaces 610 and subsequently transferred to a remote computer device via one or more of the output interfaces 620.

From the foregoing, it will be seen that the present disinfecting device can disinfect a needleless connector. When a needleless connector is at least partially inserted within a shield of the disinfecting device where it is exposed to UV light that can disinfect the external surfaces of the connector.

The present invention may be embodied in other specific forms without departing from its structures, methods, or other essential characteristics as broadly described herein and claimed hereinafter. Thus, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A device for disinfecting a needleless connector, the device comprising:
   a housing containing a UV light source, the UV light source being operably connected to a power source, the housing further comprising a receptacle through which the UV light source extends; and
   a shield forming an inner reflection chamber, the shield having a proximal portion forming a proximal opening, the proximal portion being configured to insert into the receptacle of the housing to secure the shield to the housing, the proximal opening being configured to allow the UV light source to extend into the proximal portion of the shield when the proximal portion is inserted into the receptacle, the shield further including a distal opening having a diameter sized to match a diameter of a needleless connector such that, when the needleless connector is inserted into the distal opening, the distal opening secures the needleless connector to the shield while a portion of the needleless connector extends into the inner reflection chamber.

2. The device of claim 1, wherein the shield is disposable.

3. The device of claim 1, further comprising one or more attachment features configured to selectively attach the proximal portion of the shield within the receptacle.

4. The device of claim 1, wherein the UV light source includes a UV-C LED lamp.

5. The device of claim 1, further comprising a timer electronically coupled to the UV light source to turn off the UV light source after a predetermined time period.

6. The device of claim 5, wherein the time period is approximately 5 seconds.

7. The device of claim 1, further comprising a disinfection status indicator configured to communicate a disinfection status of the needleless connector.

8. The device of claim 7 wherein the disinfection status indicator comprises one or more lights configured to indicate a disinfection status.

9. The device of claim 1, further comprising an input device for receiving an identification of at least one of the needleless connector, the shield, and the patient.

10. The device of claim 9, further comprising an output for communicating the identification of at least one of the needleless connector, the shield, and the patient.

11. The device of claim 1, wherein the shield further comprises one of a diffuser, spreader, light tube, or light pipe having a first end that is positioned within the proximal end of the shield and a second end that is positioned within the inner reflection chamber.

12. The device of claim 3, further comprising one or more ejectors disposed within the receptacle, the one or more ejectors being configured to detach the proximal end of the shield from within the receptacle.

13. The device of claim 12, wherein the one or more ejectors provide a distal force against the proximal portion of the receptacle.

14. A device for disinfecting a needleless connector, the device comprising:
   a housing containing a UV light source, the housing further comprising a receptacle through which the UV light source extends;
   a shield forming an inner reflection chamber, the shield having a proximal portion forming a proximal opening, the proximal portion being configured to insert into the receptacle of the housing to secure the shield to the housing, the proximal opening being configured to allow the UV light source to extend into the proximal portion of the shield when the proximal portion is inserted into the receptacle, the shield further including a distal opening having a diameter sized to match a diameter of a needleless connector such that, when the needleless connector is inserted into the distal opening, the distal opening secures the needleless connector to the shield while a portion of the needleless connector extends into the inner reflection chamber.

15. The device of claim 14, further comprising one or more attachment features configured to selectively attach the proximal portion of the shield within the receptacle.

16. The device of claim 15, further comprising one or more ejectors disposed within the receptacle, the one or more ejectors being configured to detach the proximal end of the shield from within the receptacle.

17. The device of claim 14, wherein the shield further comprises one of a diffuser, spreader, light tube, or light pipe having a first end that is positioned within the proximal end of the shield and a second end that is positioned within the inner reflection chamber.

18. The device of claim 14, wherein the housing includes an input interface for receiving and storing an identification of the needleless connector or an identification of a patient on which the needleless connector is used.

19. The device of claim 18, wherein the housing includes an output interface for transmitting the identification to a remote computing device.

20. A device for disinfecting a needleless connector, the device comprising:
   a housing containing a UV light source, the housing further comprising a receptacle through which the UV light source extends;
   a shield forming an inner chamber, the shield having a proximal portion forming a proximal opening, the proximal portion being configured to insert into the receptacle of the housing to secure the shield to the housing, the proximal opening being configured to allow the UV light source to extend into the proximal portion of the shield when the proximal portion is inserted into the receptacle, the shield further including a distal opening configured to allow a needleless connector to be inserted into and secured within the inner chamber;
   an input interface for receiving an identifier of a needleless connector to be disinfected by the device; and
   an output interface for transmitting the identifier to a remote computing device.

* * * * *